US006274552B1

(12) United States Patent
Tamarkin et al.

(10) Patent No.: US 6,274,552 B1
(45) Date of Patent: Aug. 14, 2001

(54) COMPOSITION AND METHOD FOR DELIVERY OF BIOLOGICALLY-ACTIVE FACTORS

(75) Inventors: Lawrence Tamarkin, Rockville; Guilio F. Paciotti, Baltimore, both of MD (US)

(73) Assignee: CytImmune Sciences, Inc., College Park, MD (US)

( * ) Notice: Subject to any disclaimer, the term of this patent is extended or adjusted under 35 U.S.C. 154(b) by 0 days.

(21) Appl. No.: 08/966,940

(22) Filed: Nov. 10, 1997

Related U.S. Application Data

(63) Continuation-in-part of application No. 08/795,962, filed on Feb. 6, 1997, now abandoned, which is a continuation of application No. 08/586,427, filed on Jan. 16, 1996, now abandoned, which is a continuation of application No. 08/215,030, filed on Mar. 18, 1994, now abandoned, which is a continuation-in-part of application No. 08/033,385, filed on Mar. 18, 1993, now abandoned.

(51) Int. Cl.$^7$ .................................................. A61K 38/00
(52) U.S. Cl. ................................ 514/12; 514/2; 514/885; 530/350; 530/351; 424/617; 424/618; 424/649; 424/85.1
(58) Field of Search .................................... 424/617, 618, 424/649, 85.1; 530/350, 351; 514/2, 12, 885

(56) References Cited

U.S. PATENT DOCUMENTS

| | | | |
|---|---|---|---|
| 2,768,958 | 10/1956 | Stewart et al. | 252/313 |
| 2,785,153 | 3/1957 | Locke et al. | 260/114 |
| 3,145,144 | 8/1964 | Ando | 167/78 |
| 3,149,036 | 9/1964 | Woodhour et al. | 167/78 |
| 3,269,912 | 8/1966 | Grase | 167/78 |
| 3,399,263 | 8/1968 | Strazdins et al. | 424/88 |
| 3,531,565 | 9/1970 | Webb et al. | 424/92 |
| 3,577,523 | 5/1971 | Stolar et al. | 424/88 |
| 3,651,211 | 3/1972 | Gillchriest et al. | 424/89 |
| 3,819,820 | 6/1974 | Lorina et al. | 424/1 |
| 3,919,413 | 11/1975 | Mebus | 424/89 |
| 3,983,228 | 9/1976 | Woodhour et al. | 424/89 |
| 4,016,252 | 4/1977 | Relyveld | 424/88 |
| 4,053,587 | 10/1977 | Davidson et al. | 424/131 |
| 4,069,313 | 1/1978 | Woodhour et al. | 424/89 |
| 4,177,263 | 12/1979 | Rosenberg et al. | 424/131 |
| 4,196,185 | 4/1980 | Focella et al. | 424/1 |
| 4,197,237 | 4/1980 | Leute et al. | 260/112 |
| 4,197,286 | 4/1980 | Rao | 424/1 |
| 4,213,964 | 7/1980 | Buckler | 424/85 |
| 4,215,036 | 7/1980 | Malley | 260/112 |
| 4,218,436 | 8/1980 | Fitzpatrick | 424/85 |
| 4,329,281 | 5/1982 | Christenson et al. | 260/112 |
| 4,330,530 | 5/1982 | Baker | 424/131 |
| 4,332,787 | 6/1982 | Homcy et al. | 424/1 |
| 4,339,437 | 7/1982 | Rosenberg et al. | 424/131 |
| 4,346,074 | 8/1982 | Gilmour et al. | 424/92 |
| 4,451,570 | 5/1984 | Royston et al. | 435/240 |
| 4,487,780 | 12/1984 | Scheinberg | 424/294 |
| 4,578,270 | 3/1986 | Csizer et al. | 424/92 |
| 4,594,325 | 6/1986 | Lundak | 435/240 |
| 4,608,252 | 8/1986 | Khanna et al. | 424/85 |
| 4,624,921 | 11/1986 | Larrick et al. | 435/172.2 |
| 4,624,923 | 11/1986 | Margel | 435/176 |
| 4,639,336 | 1/1987 | Jouquey et al. | 260/397 |
| 4,657,763 | 4/1987 | Finkelstein | 424/131 |
| 4,693,975 | 9/1987 | Kozbor et al. | 435/172.2 |
| 4,720,459 | 1/1988 | Winkelhake | 435/240.2 |
| 4,740,589 | 4/1988 | Moreno | 530/395 |
| 4,744,760 | 5/1988 | Molday | 424/3 |
| 4,753,873 | 6/1988 | Beltz et al. | 435/5 |
| 4,812,556 | 3/1989 | Vahlne et al. | 530/324 |
| 4,880,750 | 11/1989 | Francoeur | 436/501 |
| 4,882,423 | 11/1989 | Taguchi et al. | 530/380 |
| 4,906,564 | 3/1990 | Lyon et al. | 435/7 |
| 4,977,286 | 12/1990 | Nicolaou et al. | 552/4 |
| 5,017,687 | 5/1991 | Vahlne et al. | 530/324 |
| 5,019,497 | 5/1991 | Olsson | 435/7.23 |
| 5,035,995 | 7/1991 | Taguchi et al. | 435/4 |
| 5,112,606 | 5/1992 | Shiosaka et al. | 530/398.2 |
| 5,126,253 | 6/1992 | Nakanishi et al. | 435/70.21 |

FOREIGN PATENT DOCUMENTS

| | | |
|---|---|---|
| 981242 | 1/1965 | (DE) . |
| 0 044 722 | 1/1982 | (EP) . |
| 0 156 242 | 12/1985 | (EP) . |
| 0 179 483 | 4/1986 | (EP) . |
| 0 269 408 | 11/1987 | (EP) . |
| 0 667 398 | 8/1995 | (EP) . |
| 2 334 366 | 7/1977 | (FR) . |
| 2 533 827 | 9/1982 | (FR) . |
| WO 91 02078 | 2/1991 | (WO) . |
| 9421288 | * 9/1994 | (WO) . |
| WO 94/21288 | 9/1994 | (WO) . |
| WO 96/04313 | 2/1996 | (WO) . |

OTHER PUBLICATIONS

Hopkins et al., "Early Events Following the Binding of Epidermal Growth Factor to Surface Receptors on Ovarian Granulosa Cells", *Eur. J. Cell Bio.*, vol. 24, pp. 259–265 (1981).

*Primary Examiner*—Dwayne C. Jones
*Assistant Examiner*—C. Delacroix-Muirheid
(74) *Attorney, Agent, or Firm*—Kilpatrick Stockton LLP

(57) ABSTRACT

In accordance with the present invention, a composition and method is provided that allows for the administration of a biologically-active factors to a human or animal. The present invention can be used to treat a disease with a biologically-active factor or combination of biologically-active factors, or can be used to safely vaccinate a human or animal against a biologically-active factor. It can also be used as a method for the delivery of biologically-active factors for the treatment of disease. Additionally, the present invention also includes a method of targeted drug delivery for the treatment of disease through the administration of custom complexes containing of one or more biologically active factors bound to a colloidal metal where at least one of the biologically-active factors is capable of binding a high affinity receptor on a cell surface.

21 Claims, 12 Drawing Sheets

(4 of 12 Drawing Sheet(s) Filed in Color)

OTHER PUBLICATIONS

Kang et al., "Ultrastructural and Immunocytochemical Study of the Uptake and Distribution of Bacterial Lipopolysaccharide in Human Monocytes", *J. Leuk. Bio.*, vol. 48, pp. 316–332 (1990).

Morris et al., "Validation of the Biotinyl Ligand–Avidin––Gold Technique", *J. Histochem. Cytochem.*, vol. 40, pp. 711–721 (1992).

Paciotti, G.F., et al. "Interleukin–2 Differentially Effects the Proliferation of a Hormone–Dependent and a Hormone–Independent Human Breast Cancer Cell Line in Vitro and In Vivo," *Anticancer Research*, vol. 8, pp. 1233–1240 (1988).

Peters et al., "Binding and Internalization of Biotinylated interleukin–2 in Human Lymphocytes", *Blood*, vol. 76, pp. 97–104 (1990).

Fraker, et al., "Passive Immunization Against Tumor Necrosis Factor Partially Abrogates Interleukin 2 Toxicity," *The Journal of Experimental Medicine*, vol. 170, pp. 1015–1020 (1989).

Lanzavecchia, "Identifying Strategies for Immune Intervention," *Science*, vol. 260, pp. 937–944 (1993).

Paciotti, et al., "Interleukin 2 differentially effects the proliferation of a hormone–dependent and a hormone–independent human breast cancer cell line in vitro and in vivo," *Anti–Cancer Research*, vol. 8, pp. 1233–1240 (1988).

Paciotti, et al., "Interleukin 1 differentially synchronizes estrogen dependent and estrogen–independent human breast cells in $G_0/G_1$ phase of the cell cycle," *Anti–Cancer Research*, vol. 11, pp. 25–32 (1991).

Paciotti, et al., "Interleukin 1 directly regulates hormone–dependent human breast cancer cell proliferation in vitro," *Mol. Endocrinol.*, vol. 2, pp. 459–464 (1988).

Coulombe et al., "Cytochemical Demonstration of Increased Phospholipid Content in Cell Membranes in Chlorphrntermine–induced Phospholipidosis," *Journal of Histochemistry and Cytochemistry*, vol. 37, No. 2, pp. 139–147 (1989).

Hashimoto et al., "Action Site of Circulating Interleukin–1 on the Rabbit Brain," *Brain Research*, vol. 540, pp. 217–223 (1991).

Ohmann et al., "Expresion of Tumor Necrosis Factor–α Receptors on Bovine Macrophaes, Lymphocytes and Polymorphonuclear Leukocytes, Internalization of Receptor––Bound Ligand, and Some Functional Effects," *Lymphokine Research*, vol. 9, No. 1, pp. 43–58 (1990).

Balkwill et al., "The Cytokine Network", *Immun. Today*, vol. 10, No. 9, pp. 299–304 (1989).

Roitt et al., "Immunology", *Mosby*, 3rd ed., (1993).

Goldstein et al., "Cardiovascular Effects of Platelet–Activating Factor", *Lipids*, vol. 26, No. 212, pp. 1250–1256 (1991).

Hisamatsu et al., "Platelet Activating Factor Induced Respiratory Mucosal Damage", *Lipids*, vol. 26, No. 12, pp. 1287–1291 (1991).

Kirchner et al., "The Development of Neutralizing Antiboides in a Patient Receiving Subcutaneous Recombinant and Natural Interleukin–2", *Cancer*, No. 7, vol. 67, pp. 1862–1864 (1991).

Tomii et al., "Production of Anti–Platelet–Activating Factor Antibodies by the Use of Colloidal Gold as Carrier", *Jpn. J. Med. Sci. Biol.* vol. 44, pp. 75–80 (1991).

\* cited by examiner

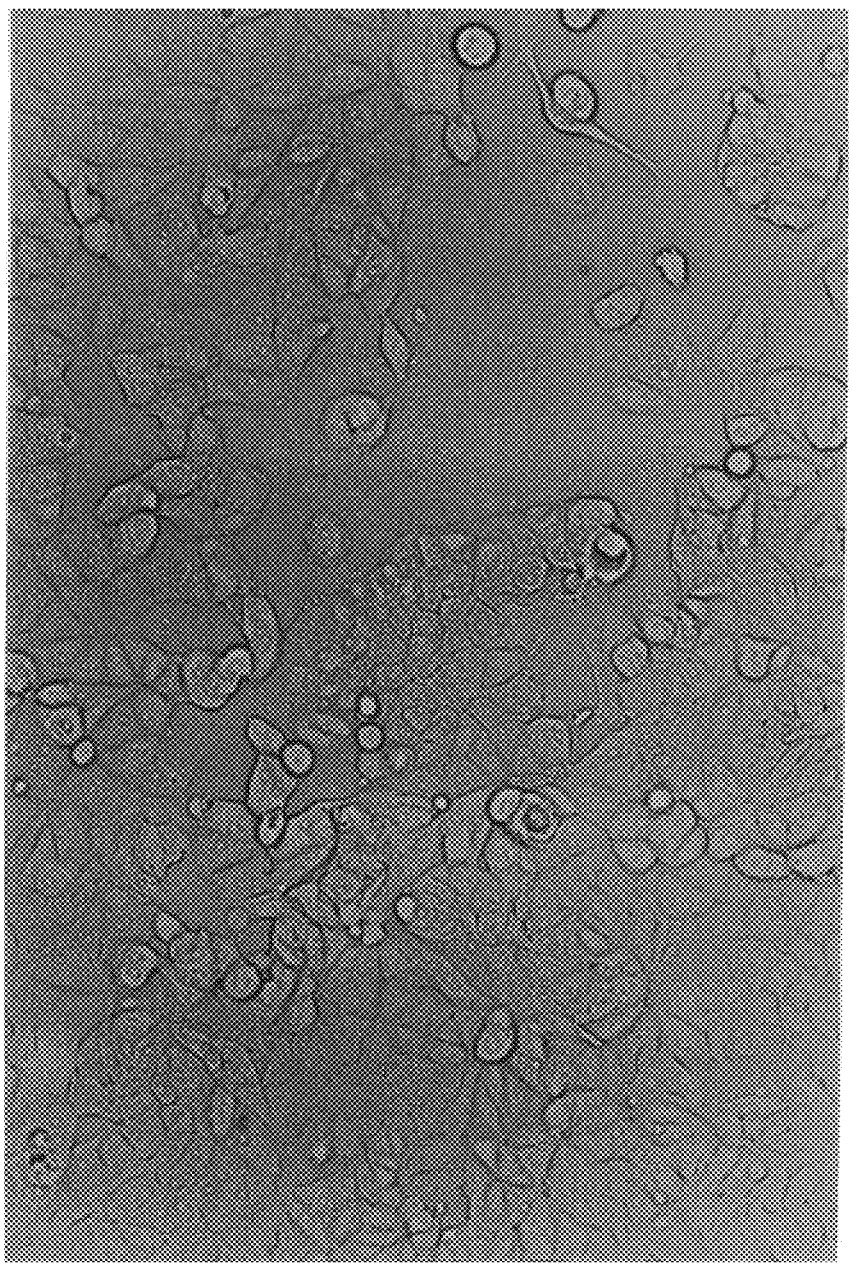
Fig_ 8A

COMPOSITION AND METHOD FOR DELIVERY OF BIOLOGICALLY-ACTIVE FACTORS

RELATED APPLICATIONS

This application is a continuation-in-part of application Ser. No. 08/795,962, filed Feb. 6, 1997, now abandoned, which is a continuation of application Ser. No. 08/586,427, filed Jan. 16, 1996, now abandoned, which is a continuation of application Ser. No. 08/215,030, filed Mar. 18, 1994, now abandoned, which is a continuation-in-part of application Ser. No. 08/033,385, filed Mar. 18, 1993, abandoned.

TECHNICAL FIELD

The present invention relates to compositions and methods for delivery of biologically-active factors, such as cytokines, growth factors, chemotherapeutic agents, nucleic acids, therapeutic agents, and other immune products. In addition, the present invention comprises vaccines which are effective in immunizing a human or animal against a biologically-active factor while reducing or eliminating the toxicity of the factor.

BACKGROUND OF THE INVENTION

Various biologically-active factors have been isolated from humans or animals which have been reported to have therapeutic efficacy. These compounds include cytokines and growth factors. However, it has been found that when these various factors are isolated and purified from natural sources or genetically engineered material, and then injected into a human or animal, they often cause severe side effects and exhibit unwanted toxicity. Because of this toxicity, it has been difficult to use the compounds therapeutically. In addition, it has been difficult to use the active compounds as antigens to produce antibodies against the molecules.

Aluminum compounds have been used to form water-insoluble antigenic substances. For example, U.S. Pat. No. 3,577,523, issued to Stolar, et al., discloses the combination of aluminum stannate with antigenic extracts to form water-insoluble slow release antigenic substances. More generally, the Stolar, et al. patent discloses the use of antigenic depot agents incorporating water-insoluble antigenic substances that slowly release active agents that are absorbed without adverse systemic reactions or other adverse side effects.

Metals have also been used in capsular polysaccharide metal complex vaccines. For example, in U.S. Pat. No. 4,740,589, issued to Moreno, a bacterial capsular polysaccharide constituent was complexed with a metal, preferably aluminum or ruthenium, for the prophylaxis and treatment of bacterial diseases. This patent also discloses the formulation of a three component complex which contains a polysaccharide, a metal, and a third constituent of bacterial outer-membrane protein. The '589 patent discloses that the complex contains a weight percentage of lipopolysaccharide "insufficient to produce significant toxic effects", the weight percentage being generally 1% or less. Finally, the disclosure in the '589 patent application is limited to the use of the complexes for prophylaxis and treatment of bacterial diseases. U.S. Pat. No. 3,269,912, issued to Grase, discloses a depot vaccine comprising a finely divided aluminum oxide, either aluminum oxide or aluminum oxide aerosol having had absorbed thereon at least one antigen derived from a virus, bacteria, or ectotoxoid, dispersed in an aqueous medium. The '912 patent also discloses that the vaccine forms a colloidal dispersion of the individual spherical crystals of aluminum oxide in the solution.

Selected metals have also been used as components of stable adjuvant emulsion compositions. It is known in the art that aluminum, as the monostearate, or in the form of hydrated salts of fatty acids, are emulsifying agents, or stabilizers of the emulsion in the vaccine composition.

However, substantial need exists for a therapeutically effective composition with reduced toxicity, that may be used in therapies for a wide range of immune diseases, cancers, viral diseases and bacterial diseases. In addition, there is a need for a composition that can reduce the toxicity of normally toxic biologically-active compositions so that the compounds can be used as vaccines in the human or animal.

Current therapies for the treatment of diseases and pathological conditions, including genetic diseases, congenital diseases and acquired diseases such as bacterial infections, viral infections, cancer, immune deficiency diseases, autoimmune diseases, psychiatric diseases, cardiovascular diseases, reproductive dysfunction, somatic growth dysfunction, stress related diseases, muscular dystrophy, osteoporosis, ocular diseases, allergies, and transplantation rejection, require administration of toxic doses of biologically-active factors that have widespread effects throughout the body. These therapies are not specifically targeted to the affected organs for direct delivery of a biologically active factor.

Current treatments for cancer include administration of chemotherapeutic agents and other biologically active factors such as cytokines and immune factors. The administration of chemotherapeutic agents to the entire body creates toxic and adverse side effects such as organ damage, loss of senses such as taste and feel, and hair loss. Many chemotherapeutic agents are designed to kill rapidly dividing cells which indescriminately effects the hematopoetic system and the gastrointestinal system leading to changes in blood and immune cells, vomiting, gastric distress and weight loss. Administration of immune factors, such a cytokines, to the entire body system leads to activiation of unwanted immune responses and inhibition of other immune functions. Such therapies provide treatment for the condition, but come with a wide array of side effects that must then be treated. In addition, bolus administration of a drug may not be optimal because of rapid clearance.

Other types of biologically active factors, based on nucleic acids, are being developed for therapeutic use to treat diseases and pathological conditions. Examples of such therapeutic uses include, gene replacement, antisense gene therapy, triplex gene therapy and ribozyme-based therapy. However, to be successful, an effective means for the delivery of the therapeutic agent across cellular, nuclear and microorganismal membranes is required.

The recent advent of technology, and advances in our ability to understand the structure and function of many genes makes it possible to selectively turn off or modify the activity of a given gene. Alteration of gene activity can be accomplished many ways. For example, oligonucleotides that are complementary to certain gene messages or viral sequences, known as "antisense" compounds, have been shown to have an inhibitory effect against viruses. By creating an antisense compound that hybridizes with the targeted RNA message of cells or viruses the translation of the message into protein can be interrupted or prevented. In this fashion gene activity can be modulated.

The ability to deactivate specific genes provides great therapeutic benefits. For example, it is theoretically possible to fight viral diseases with antisense RNA and DNA molecules that seek out and destroy viral gene products. In tissue culture, antisense oligonucleotides have inhibited infections by herpes-viruses, influenza viruses and the human immunodeficiency virus that causes AIDS. It may also be possible to target antisense oligonucleotides against mutated oncogenes. Antisense technology also holds the potential for regulating growth and development. However, in order for the gene therapy to work, antisense therapeutic compounds must be delivered across cellular plasma membranes to the cytosol.

Gene activity is also modified using sense DNA in a technique known as gene therapy. Defective genes are replaced or supplemented by the administration of "good" or normal genes that are not subject to the defect. The administered normal genes which insert into a chromosome, or may be present in extracellular DNA, produce normal RNA, which in turn leads to normal gene product. In this fashion gene defects and deficiencies in the production of gene product may be corrected. Still further gene therapy has the potential to augment the normal genetic complement of a cell. For example, it has been proposed that one way to combat HIV is to introduce into an infected person's T cells a gene that makes the cells resistant to HIV infection. This form of gene therapy is sometimes called "intracellular immunization." Genetic material such as polynucleotides may be administered to a mammal to elicit an immune response against the gene product of the administered nucleic acid sequence. Such gene vaccines elicit an immune response in the following manner. First, the nucleic acid sequence is administered to a human or animal. Next, the administered sequence is expressed to form gene product within the human or animal. The gene product inside the human or animal is recognized as foreign material and the immune system of the human or animal mounts an immunological response against the gene product. However, this approach currently is not feasible due to a lack of effective gene delivery systems that facilitate the delivery of genetic material across both cellular and nuclear membranes.

Finally, gene therapy may be used as a method of delivering drugs in vivo. For example, if genes that code for therapeutic compounds can be delivered to endothelial cells, the gene products would have facilitated access to the blood stream. Currently, one method for gene delivery to cells is ex vivo and then reintroduction to the animal. Alternatively, gene therapy has been accomplished in vivo by the injection of naked DNA, DNA-containing liposomes, and the injection of viral or bacterial DNA-containing vectors.

Retroviral vectors can be used to deliver genes ex vivo to isolated cells, which are then infused back into the patient. However, retroviral vectors have some drawbacks, such as being able to deliver genes only to dividing cells, random integration of the gene to be delivered, potentially causing unwanted genetic alterations, and possibly reverting back to an infectious wild-type retroviral form. Another drawback of antisense gene therapy is that it is effective at the messenger RNA level, which means that antisense oligonucleotides must be introduced in a quantity to interact with all or a substantial number of the mRNA in the cytosol, and that such treatment is only effective during active synthesis of mRNA. Further, the oligonucleotides must be maintained at this high quantity level throughout mRNA synthesis to be effective over time.

Newly developed "triplex DNA" technology represents an improvement in gene regulation. Triplex DNA technology utilizes oligonucleotides and compounds that specifically bind to particular regions of duplex DNA, thereby inactivating the targeted gene. An advantage of triplex DNA technology is that only a single copy of the oligonucleotide or compound is required to alter gene expression because the binding is at the DNA level, not the MRNA level. A drawback of triplex DNA technology, however, is that the oligonucleotide or compound must pass through not only the cellular membrane, but also the microbial membrane in the case of treating microbial infections, or the nuclear membrane in the case of altering eukaryotic gene function or expression of foreign DNA integrated into chromosomal DNA.

Another emerging technology relates to the therapeutic use of ribozymes for the treatment of genetic disorders. Ribozymes are catalytic RNA molecules that consist of a hybridizing region and an enzymatic region. Ribozymes may in the future be engineered so as to specifically bind to a targeted region of nucleic acid sequence and cut or otherwise enzymatically modify the sequence so as to alter its expression or translation into gene product.

There is a great need, therefore, for improved delivery systems for genetic material such as genes, polynucleotides, and antisense oligonucleotides that can be used in gene therapy. More specifically, there is a need for compositions that can facilitate the transport of genetic compounds and other drugs and therapeutic compounds across cellular membranes.

SUMMARY OF THE INVENTION

The present invention satisfies the above-described needs by providing effective compositions containing normally toxic compounds that, when in combination with a colloidal metal, result in significantly reduced toxic side effects. Generally, the composition of the present invention comprises an admixture of a colloidal metal, such as gold chloride ($HAuCl_4$) in combination with a substance which normally is toxic to a human or animal or a substance capable of producing an immune response, wherein the composition when administered to a human or animal is less or non-toxic.

A method of use of the above composition comprises administering to a human or animal an effective amount of a composition comprising a colloidal metal, such as $HAuCl_4$, in combination with a substance which normally is toxic to a human or animal capable of producing an immune response, wherein the composition, when administered to a human or animal, is less toxic or non-toxic.

The use of colloidal metals in combination with normally toxic biologically-active factors may be used in the treatment of bacterial infections, viral infections, cancer and immune disease therapies, including, but not limited to, autoimmune diseases, such as rheumatoid arthritis and acquired immune deficiency. Current therapies which consist of administering factors such as interleukins to a human or animal are marginally effective but produce significant, toxic side effects. Also, the occurrence of toxic side effects limits the amount of biologically-active factors that may be administered, and therefore limits the efficacy of the therapy. Additionally, some otherwise therapeutic compounds are not used at all due to their toxicity. The combination of a colloidal metal with such biologically-active factors reduces toxicity while maintaining the therapeutic effectiveness.

The present invention also provides a method for treatment of diseases by administration of one or more biologically-active factors bound to a colloidal metal particle. The biologically-active factor is released in vivo from the colloidal metal to deliver an effective dose of the biologically-active factor over an extended period of time.

The advantage of this delivery system is that lower doses of the biologically-active factor are delivered to the patient over a longer period of time. This results in reduced toxicity and fewer side-effects.

The in vivo release of the biologically-active factor from the colloidal metal is thought to be controlled by two factors: equilibrium kinetics and the amount of biologically-active factor initially bound to the colloidal metal. Equilibrium kinetics control the release of the biologically-active factor through the dilution of the factor in the body. The amount of biologically-active factor released is also directly proportional to the amount of biologically-active factor initially bound to the colloid metal particle.

Additionally, the present invention provides a method for the treatment of diseases through the targeted delivery of biologically-active factors. The method comprises administration of a composition containing a custom complex having one or more biologically-active factors bound to colloidal gold. Preferably, the composition contains at least two biologically-active factors where one of the factors is a target molecule capable of binding receptors on a cell surface. Once the composition is bound to the cell surface, the composition is internalized by the cell. After internalization, the biologically-active factors are released from the colloid metal. One advantage of this method is that smaller amounts of biologically-active factor can be used than that with previously known methods because the factor is transported across the cell membrane without disruption of the cell membrane. This method also provides cellular specificity, and, once bound to the cell, the gold-bound, biologically-active factor may serve as an immobilized source of releasable biologically-active factor—a constant release depot.

Accordingly, it is an object of the present invention to provide a composition that is capable of reducing the toxicity of biologically-active factors.

A further object of the present invention is to provide a composition containing higher concentrations of biologically-active factors than are currently utilized due to the toxicity of the substances.

Another object of the present invention is to provide a composition to be used in cancer therapies which results in reduced side effects from toxicity.

Yet another object of the present invention is to provide a composition for immune disease therapy which results in reduced side effects from toxicity.

Another object of the present invention is to provide a therapeutic method for immune disease therapy which results in reduced toxic side effects and maintains its beneficial effects.

Yet another object of the present invention is to provide a method of vaccinating a human or animal against a normally toxic biologically-active factor.

A further object of the present invention is to provide a method for the slow release of biologically-active factors.

Another object of the present invention is to provide a therapeutic method for the treatment of cancer through the extended in vivo release of biologically-active factors.

Another object of the present invention is to provide a therapeutic method for the treatment of immune deficient diseases through the extended in vivo release of biologically-active factors.

Another object of the present invention is to provide custom complexes composed of one or more biologically-active factors bound to a colloidal metal for the treatment of diseases.

It is another object of the present invention is to provide custom complexes composed of one or more biologically-active factors bound to a colloidal metal for the treatment of cancer, both solid tumors as well as blood-borne cancers.

Yet another object of the present invention is to provide custom complexes composed of one or more biologically-active factors bound to a colloidal metal for the treatment of autoimmune diseases.

Still another object of the present invention is to provide custom complexes composed of one or more biologically-active factors bound to a colloidal metal for the treatment of hormone deficiency diseases.

It is another object of the present invention is to provide custom complexes composed of one or more biologically-active factors bound to a colloidal metal for the treatment of hormone abnormalities due to hypersecretion.

It is yet another object of the present invention is to provide custom complexes composed of one or more biologically-active factors bound to a colloidal metal for the treatment of infectious diseases, such as septic shock.

A further object of the present invention is to provide custom complexes composed of one or more biologically-active factors bound to a colloidal metal for the treatment of genetic diseases.

It is another object of the present invention is to provide custom complexes composed of one or more biologically-active factors bound to a colloidal metal for the treatment of immune deficiency diseases.

A further object of the present invention is to provide custom complexes composed of one or more biologically-active factors where at least one of the biologically-active factors is a target molecule capable of binding a high affinity receptor on the cell surface.

Yet another object of the present invention is to provide a method of delivering a biologically-active factor to the interior of a cell.

Another object of the present invention is to provide a method of delivering a biologically-active factor to the interior of a cell by administering a composition containing a custom complex composed of one or more biologically-active factors bound to a colloidal metal where at least one of the biologically-active factors is a target molecule capable of binding a high affinity receptor on a cell surface.

Yet another object of the present invention is a therapeutic method for the treatment of cancer by administering a composition containing a custom complex comprised of one or more biologically-active factors bound to a colloidal metal where at least one of the biologically-active factors is a target molecule capable of binding a high affinity receptor on a cell surface.

Yet another object of the present invention is a therapeutic method for the treatment of immune deficiency diseases by administering a composition containing a custom complex comprised of one or more biologically-active factors bound to a colloidal metal where at least one of the biologically-active factors is a target molecule capable of binding a high affinity receptor on the cell surface.

These and other objects, features and advantages of the present invention will become apparent after a review of the following detailed description of the preferred embodiment.

This patent contains at least one color photograph. Copies of this patent with the color photographs will be provided by the Patent and Trademark Office upon request and payment of the necessary fee.

BRIEF DESCRIPTION OF THE DRAWINGS

FIGS. 8a–d illustrate the internalization of colloidal gold-bound IL-1β by MCF-7 cells.

DETAILED DESCRIPTION

Figure 1:
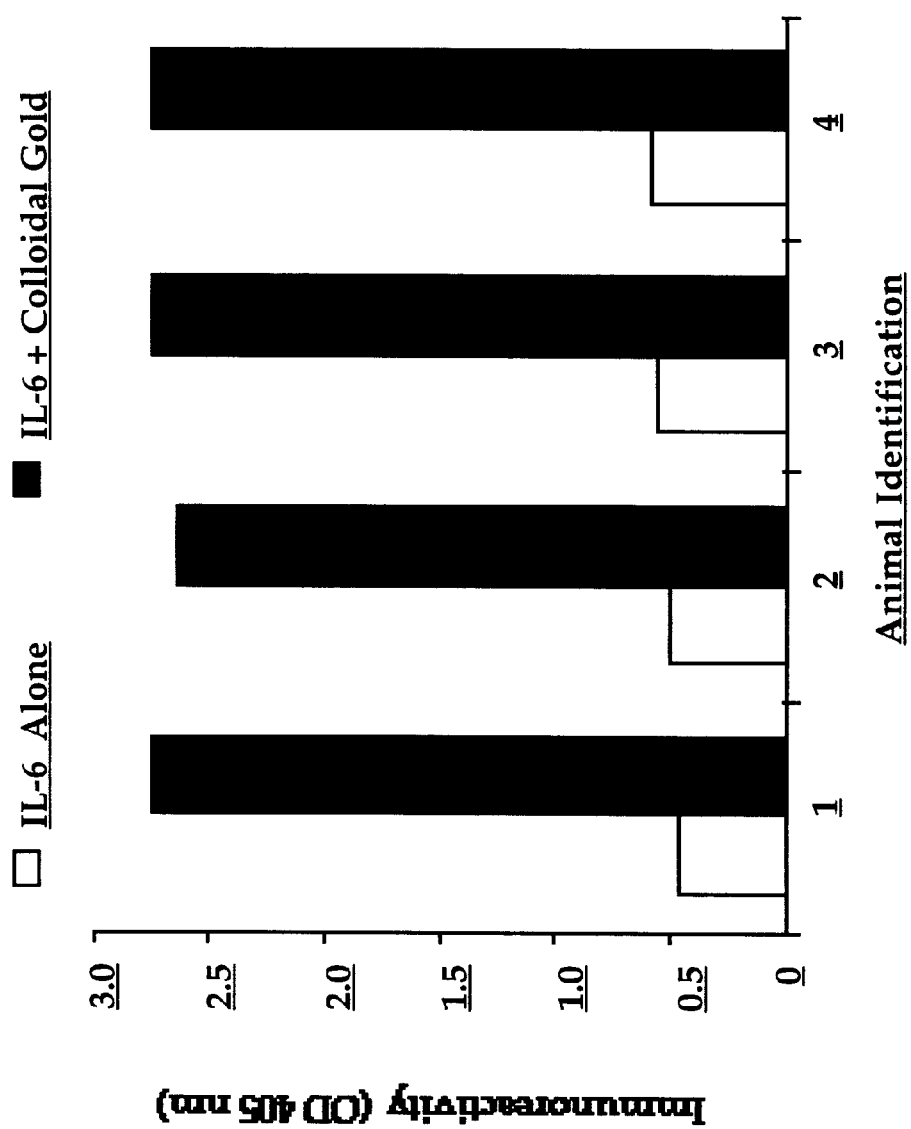
FIG. 1 illustrates the effect of colloidal gold on the generation of a murine-anti-murine IL-6 antibody response.
Figure 2:
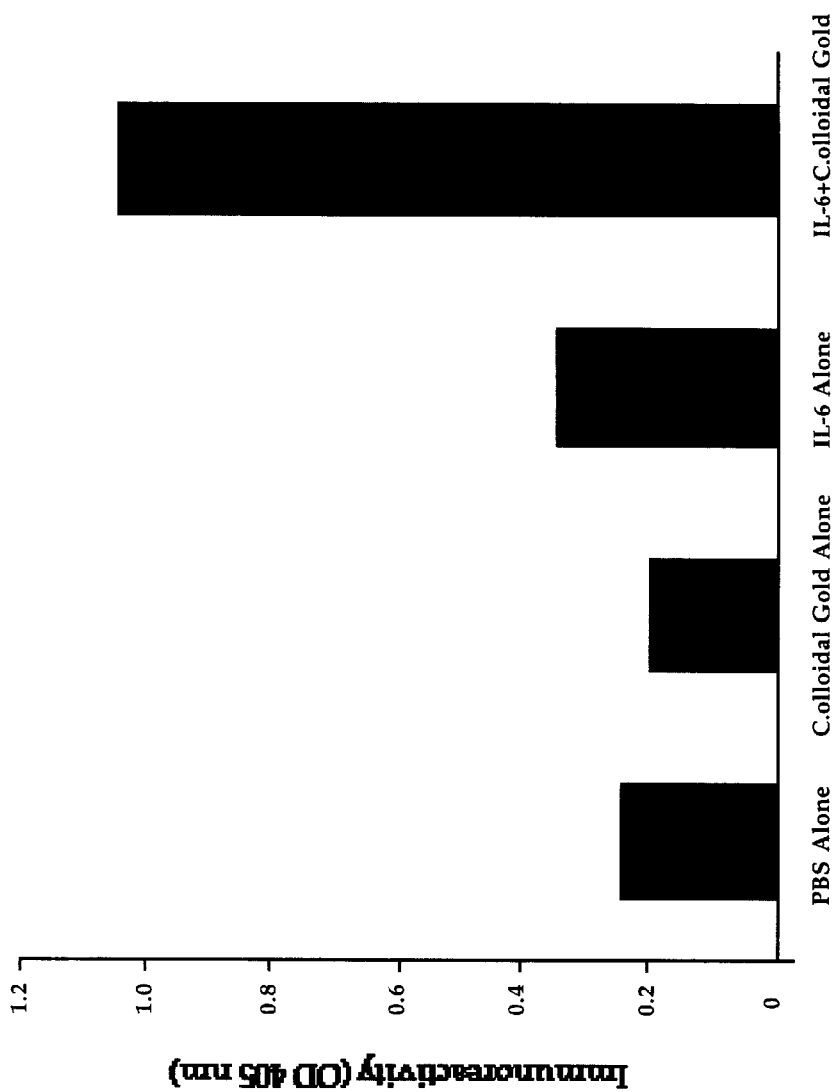
FIG. 2 illustrates the increase in immunoreactivity of murine-anti-murine IL-6 antibody response in cells activated with IL-6 bound to colloidal gold over those activated with IL-6 or colloidal gold alone.

The terms "toxic reaction," and "toxicity," as used herein, include, but are not limited to, the following responses of an animal or human: fever; edema, including cerebral edema; psychosis; autoimmune diseases; hemorrhage; shock, including hemorrhagic shock; sepsis; cachexia; or death. The term "colloidal metal", as used herein, includes any water-insoluble metal particle or metallic compound dispersed in liquid water (a hydrosol). The term "biologically-active factors" includes, but is not limited to, Interleukin-1 ("IL-1"), Interleukin-2 ("IL-2 "), Interleukin-3 ("IL-3"), Interleukin-4 ("IL-4"), Interleukin-5 ("IL-5"), Interleukin-6 ("IL-6 "), Interleukin-7 ("IL-7"), Interleukin-8 ("IL-8"), Interleukin-10 ("IL-10"), Interleukin-i 1 ("IL-11"), Interleukin-12 ("IL-12"), Interleukin-13 ("IL-13"), Interleukin-15 ("IL-15"), Interleukin-16 ("IL-16"), Interleukin-17 ("IL-17"), Interleukin-18 ("IL-18"), lipid A, phospholipase A2, endotoxins, staphylococcal enterotoxin B and other toxins, Type I Interferon, Type II Interferon, Tumor Necrosis Factor ("TNFα"), Transforming Growth Factor-β ("TGF-,β"), Lymphotoxin, Migration Inhibition Factor, Granulocyte-Macrophage Colony-Stimulating Factor ("CSF"), Monocyte-Macrophage CSF, Granulocyte CSF, vascular epithelial growth factor ("VEGF"), Angiogenin, transforming growth factor ("TGFα"), heat shock proteins, carbohydrate moieties of blood groups, Rh factors, fibroblast growth factor, hormones, such as growth hormone, insulin, glucogen, parathyroid hormone, leutinizing hormone, follicle stimulating hormone, and leutinizing hormone releasing hormone, cell surface receptors, antibodies, chemotherapeutic agents, and other inflammatory and immune regulatory proteins, nucleotides, DNA, RNA, sense, antisense, cancer cell specific antigens; such as MART, MAGE, BAGE, and HSPs; and immunotherapy drugs, such as AZT.

The term "target molecule" includes, but is not limited to, interleukin-1 ("IL-1"), interleukin-2 ("IL-2"), interleukin-3 ("IL-3"), interleukin-4 ("IL-4"), interleukin-5 ("IL-5"), interleukin-6 ("IL-6"), Interleukin-7 ("IL-7"), interleukin-8 ("IL-8"), Interleukin-10 ("IL-10"), Interleukin-11 ("IL-11"), interleukin-12 ("IL-12"), interleukin-13 ("IL-13"), Type I interferon, Type II interferon, tumor necrosis factor ("TNFα"), transforming growth factor-β ("TGF-β"), vascular epithelial growth factor ("VEGF"), transforming growth factor ("TGFα"), receptor proteins, glucose, glycogen, phosphoipids, and monoclonal and/or polyclonal antibodies.

The present invention comprises a composition and method for administering normally toxic biologically-active factors to a human or animal. Generally, the composition according to the present invention comprises an admixture of a colloidal metal in combination with a substance which normally is toxic to a human or animal capable of producing an immune response, wherein the composition, when administered to a human or animal, is less toxic or non-toxic to the human or animal. The composition optionally includes a pharmaceutically-acceptable carrier, such as an aqueous solution, or excipients, buffers, antigen stabilizers, or sterilized carriers. Also, oils, such as paraffin oil, may optionally be included in the composition.

The composition of the present invention can be used to vaccinate a human or animal against biologically-active factors which are normally toxic when injected. In addition, the present invention can be used to treat certain diseases with cytokines or growth factors. By admixing the biologically-active factors with the colloidal metal before administering them to the human or animal, the toxicity of the biologically-active factor is reduced or eliminated thereby allowing the factor to exert its therapeutic effect.

Current therapies which comprise administering biologically-active factors to a human or animal are somewhat effective yet produce significant toxic side effects. Further, the toxic side effects limit the amount of antigen that may be administered, and therefore limit the efficacy of the therapy. Additionally, the toxicity of some biologically-active factors precludes their use in such therapies. The combination of a colloidal metal with such biologically-active factors reduces toxicity while maintaining or increasing the therapeutic results thereby improving the efficacy as higher concentrations of biologically-active factors may be administered, or by allowing the use of combinations of biologically-active factors. The use of colloidal metals in combination with biologically-active factors therefore allows the use of higher concentrations of biologically-active factors or formerly unusable toxic substances, to be administered to humans or animals.

The colloidal metal may for example be selected from the metals in groups 'IA, IB, "B and '"B of the periodic table, as well as the transition metals, especially those of group VIII. Preferred metals include gold, silver, aluminum, ruthenium, zinc, iron, nickel and calcium. Other suitable metals may also include the following in all of their various oxidation states: lithium, sodium, magnesium, potassium, scandium, titanium, vanadium, chromium, manganese, cobalt, copper, gallium, strontium, niobium, molybdenum, palladium, indium, tin, tungsten, rhenium, platinum, and gadolinium. The metals are preferably provided in ionic form, (preferably derived ;from an appropriate metal compound) for example the $Al^{3+}$, $Ru^{3+}$, $Zn^{2+}$, $Fe^{3+}$, $Ni^{2+}$ and $Ca^{2+}$ ions. A preferred metal is gold, particularly in the form of $Au^{3+}$. An especially preferred form of colloidal gold is $HAuCl_4$ (E-Y Laboratories, Inc., San Mateo, Ca.). Another preferred metal is silver, particularly in a sodium borate buffer, having the concentration of between approximately 0.1% and 0.001%, and most preferably as approximately a 0.01% solution. The color of such a colloidal silver solution is yellow and the colloidal particles range from 1 to 40 nanometers. Such metal ions may be present m the complex alone or with other inorganic ions.

The biologically-active factor may be bound to the colloidal metal by any method. One preferred method is to reconstitute the biologically-active factor, such as a cytokine, in water at a pH of 1 to 3 pH units above its isoelectric point, pI. Approximately 200 to 500 μg of the biologically-active factor is then incubated with colloidal metal. The duration of the incubation is not critical, but is preferably from 18 to 36 hours.

Following incubation, the colloidal metal bound biologically-active factor is optionally stabilized by incubating it overnight with 1% by volume of a 1–100% solution of polyethylene glycol (PEG). Alternatively, cysteine, phospholipids, Brij 58, or sulfhydryl-containing compounds can be used to stabilize the colloidal metal bound biologically-active factor. The colloidal metal solution is then centrifuged, followed by optional stabilization of the resulting pellet by incubation with cysteine, phospholipids, sulfhydryl-containing compounds, or a 1% solution of human serum albumin (HSA) in protein reconstitution buffer. Typically, between 90 and 95% of the biologically-active factor is bound by this method, as determined by immunoassay measurement of the unbound biologically-active factor in the supernatant.

Binding of a biologically-active factor in this manner changes the physical properties of the colloidal metal. Prior to binding, the colloidal metal cannot be filtered through a 0.22 micron filter. After binding, the colloidal complex is easily filtered. This difference suggests that the metal is no longer present as a colloid, but as an ionic solution.

The amount of colloidal metal that is used in the present invention is between approximately 0.001 mg/ml and 1.0 mg/ml with the more preferred amount of colloidal metal being between approximately 0.01 mg/ml and 0.1 mg/ml. The amount of the composition according to the present invention to be administered to humans or animals varies according to the disease to be treated, the biologically-active factor or factors used in the therapy, the species involved, and the physical state of the individual to be treated.

One embodiment of the present invention is to use the biologically-active factor associated with the colloidal metal as a vaccine preparation. Among the many advantages of such a vaccine, is the reduction of toxicity of normally toxic factors. The vaccine against biologically-active factors may be prepared by any method. One preferred method for preparing a vaccine against biologically-active factors is to admix the selected biologically-active factor with the colloidal metal in a salt-free medium, preferably deionized water. The salt-free medium may optionally be buffered with, for example, Tris buffer. In one embodiment of the invention, the colloidal metal solution is diluted 1:1 with the solution of biologically-active factors.

The medium should preferably not contain sodium ions. A colloidal gold solution has a light pink color, this color should not change when adding the solution containing the biologically-active factors. If the colloidal gold solution turns from pink to purple, this indicates that the gold has precipitated and cannot be reconstituted for effective immunization. The shelf-life of an admixture of colloidal gold and biologically-active factor(s) is approximately 24 hours.

The admixture of biologically-active factors and colloidal metal is then injected into an appropriate animal. For example, rabbits weighing between approximately two to five kilograms suffered no noticeable side-effects after they were administered, every two weeks, a composition comprising colloidal gold and 1 mg of cytokine, either IL-1 or IL-2 . Because the biologically-active factor is not toxic when administered according to the present invention, the optimal quantity of antigen can be administered to the animal. The compositions according to the present invention may be administered in a single dose or they may be administered in multiple doses, spaced over a suitable time scale to fully utilize the secondary immunization response. For example, antibody titers have been maintained by administering boosters once a month.

The vaccine may further comprise a pharmaceutically acceptable adjuvant, including, but not limited to Freund's complete adjuvant, Freund's incomplete adjuvant, lipopolysaccharide, monophosphoryl lipid A, muramyl tripeptide, liposomes containing lipid A, alum, muramyl tripeptidephosphatidylethanoloamine, keyhole and limpet hemocyanin. A preferred adjuvant is Freund's incomplete adjuvant, which preferably is diluted 1:1 with the mixture of colloidal metal and biologically-active factor.

The amount of biologically-active factor used in the present invention is between approximately 200 $\mu$g and 500 $\mu$g of protein bound in 25 ml of gold, which is then sequentially concentrated to 200 $\mu$l. Ideal concentrations to be administered in vivo are approximately 6.5 mg of protein/kg body weight. The actual amount will vary depending upon the particular patient and condition to be treated. The amount of bound biologically-active factor released in the body depends upon the amount of protein initially bound to the colloidal metal and the total concentration of protein administered to the patient.

The method of use of the composition comprises administering to a human or animal an effective amount of the composition comprising a colloidal metal admixed with a biologically-active factor or factors, wherein the composition when administered to a human or animal, is less or non-toxic. The composition according to the present invention can be administered as a vaccine against a normally toxic substance or can be a therapeutic agent wherein the toxicity of the normally toxic agent is reduced thereby allowing the administration of higher quantities of the agent over longer periods of time.

In practicing this invention, the process by which the composition is administered is not considered critical. The routes that the composition may be administered according to this invention include, but are not limited to, subcutaneous, intramuscular, intraperitoneal, oral, and intravenous routes. A preferred route of administration is intravenous. Another preferred route of administration is intramuscular.

It is known that Interleukin-2 (IL-2 ) displays significant therapeutic results in the treatment of renal cancer. However, the toxic side effects result in the death of a significant number of the patients. In contrast, if IL-2 is mixed with colloidal gold, little or no toxicity is observed and a strong immune response occurs. The doses previously used for IL-2 therapy have been on the order of $21\times10^6$ units of IL-2 per 70 kg man per day ($7\times10^6$ units of IL-2 per 70 kg man TID). One unit equals approximately 50 picograms, 2 units equals approximately 0.1 nanograms, so $20\times10^6$ units equals 1 milligram. In one embodiment of this invention, the amount of IL-2 that has been given to rabbits is approximately 1 mg per 3 kg rabbit. In effect, the studies of the effects of the administration of biologically-active factors described herein have included doses of more than 20 times higher than that previously given to humans.

In another embodiment, where IL-2 (1 mg per 3 kg animal) was administered to 3 rabbits every third day for a two-week period, all the animals appeared to be clinically sick, and two of the animals died from the apparent toxic effects of the IL-2. When the same dose of IL-2 was combined with colloidal gold and then administered to three rabbits for the same two-week period, no toxicity was observed and a significant antibody response resulted in all three animals. A "positive antibody response" as used herein is defined as a three to fourfold increase in specific antibody reactivity, as determined by direct ELISA, comparing the post-immunization bleed with the preimmunization bleed. A direct ELISA is done by binding IL-2 onto a microtiter plate, and determining the quantity of IgG bound to the IL-2 on the plate, by goat anti-rabbit IgG conjugated to alkaline phosphatase. Therefore, it is thought that the biological effects of the IL-2 remain. As the toxicity effects have been minimized, larger concentrations of IL-2 may be administered if necessary where a larger, more effective immune response is required.

In another embodiment the invention encompasses a method for treating a disease by administering a composition comprising one or more biologically-active factors bound to a colloidal metal. After administration, the biologically-active factor is released from the colloidal metal. The release is not simply a function of the circulation time, but is controlled by equilibrium kinetics.

When the colloidal metal:biologically-active factor complex ("complex") was incubated with cells for 25 days, it was found that only 5% of the biologically-active factor was released from the colloidal metal. Thus, circulation time alone does not explain the mechanism through which the biologically-active factor is released from the complex in vivo. However, it has been found that the amount of biologically-active factor released is, in part, dependent upon the concentration of the complex in the body. When various dilutions of the complex were analyzed (CytELIZA assay system CytImmune Sciences, Inc., College Park, Md.), it was found that the more dilute solutions of the complex released a significantly greater amount of biologically-active factor. For example, there was essentially no release of biologically-active factor in a 1:100 dilution of the complex, whereas over 35,000 pg. of biologically-active factor was released in a 1:100,000 dilution of the same sample of complex.

Therefore, the lower the concentration of the complex, the greater the amount of biologically-active factor released. The higher the concentration of the complex, the lower the amount of biologically-active factor released. Thus, due to the continuous in vivo dilution of the complex by blood and extracellular fluids, it is possible to achieve the same therapeutic effect by administering a lower dose of biologically-active factor to a patient than can be administered by previously known methods.

It has also been found that the amount of biologically-active factor released from the colloidal metal:biologically active factor complex is dependent upon the amount of biologically-active factor initially bound to the colloidal metal. More biologically-active factor is released in vivo from complex having a greater amount of biologically-active factor initially bound. Thus, the skilled artisan is able to control the amount of biologically-active factor delivered by varying the amount of biologically-active factor initially bound to the colloidal metal.

These combined properties provide a method by which a large amount of biologically-active factor can be bound to a colloidal metal, thereby rendering the biologically-active factor less toxic than if administered alone. Then, a small amount of the colloidal metal:biologically-active complex can be administered to a patient resulting in the slow release of the biologically-active factor from the complex. This method provides an extended, low dose of the biologically active/therapeutic factor for the treatment of diseases such as cancer and immune diseases.

A further embodiment of the present invention is the production of custom complexes in which one or more biologically-active factors are bound to the same colloid metal particle where at least one of the biologically-active factors is capable of binding a receptor on a cell membrane. This factor is defined herein as a "targeting molecule". The biologically-active factors may be bound to the colloidal metal in any combination. For example, a targeting and effector complex can be produced by binding a cytokine and a cytokine/receptor to the colloid metal particle. Alternatively, a gene delivery system for genetic therapy can be produced by binding a nucleotide and a cytokine/receptor to the colloid metal particle. A therapeutic custom complex can be produced by binding a chemotherapeutic agent and a cytokine/receptor to the colloidal metal particle. For example, an antibody to a cancer antigen can be the target molecule and can be bound to the colloidal metal along with a chemotherapeutic agent. The chemotherapeutic agent is normally a substance that is toxic to cells. In delivering the chemotherapeutic agent to a target cell, such as a cancer cell, low concentrations of the chemotherapeutic agent can be used thereby reducing the systemic toxicity of the chemotherapeutic agent.

Another embodiment of the present invention is to use the binding of two or more biologically-active factors to the same colloidal metal particle as a method for binding one molecule to a cell surface receptor, while the second molecule is released into the extracellular space proximal to the target cell. Such a slow release depot serves to deliver biologically active molecules to their specific site of action.

Yet another embodiment of the present invention is to use the binding of two or more biologically-active factors to the same colloidal metal particle as a method for using specific molecule transport mechanism of one of these molecules to cross biological barriers, which then carries the second molecule along with the complex. Molecules, such as glucose, which have a specific blood-brain transport system is bound to the colloidal metal, along with another biologically active molecule. The active transport of glucose across the blood-brain barrier serves as a conduit for biologically-active factors, which in and of themselves are unable to cross this biological barrier. This complex then serves as a vehicle for the delivery of therapeutic molecules to the brain.

These custom complexes are useful for the treatment of a number of diseases including, but not limited to, cancer, both solid tumors as well as blood-borne cancers, such as leukemia; autoimmune diseases, such as rheumatoid arthritis; hormone deficiency diseases, such as osteoporosis; hormone abnormalities due to hypersecretion, such as acromegaly; infectious diseases, such as septic shock; genetic diseases, such as enzyme deficiency diseases (e.g., inability to metabolize phenylalanine resulting in phenylketanuria); and immune deficiency diseases, such as AIDS.

At least one of the biologically-active factors bound to the colloidal metal is a target molecule which binds to a receptor on the cell surface. Different types of cells can be target through the use of different biologically-active factors. For example, the simultaneous binding of a cancer cell marker, such as MART and a chemotherapeutic agent, such as methotrexate. Another example is binding of IL-2 and an anti-viral compound for the treatment of virally infected T-cells in AIDS patients. Another example is the delivery of two biologically-active factors to the site of one response cell, such as in cancer immunotherapy. Yet another example is the binding of a bacterial coat protein to the colloidal metal in conjunction with an antibiotic, allowing for the targeted delivery of the drug at lower doses than typical systemic administration.

The biologically-active factors are bound to the colloidal metal to form a custom complex that will target one or more cell types. When the custom complex is administered to a patient, the target molecule binds to the corresponding receptor on the cell surface. After binding, the entire colloidal metal:biologically-active factor complex is internalized within the cell. Once inside the cell, the biologically-active factor is released from the colloidal metal.

This targeted delivery system has a number of advantages over the prior art. First, it requires lower doses of biologically-active factor to treat a particular condition than is required by conventional therapies. This is because the biologically-active factor is delivered directly to the cells upon which it has activity rather than the random contact which occurs in conventional therapies.

Second, because smaller doses of the biologically-active factor can be used and because of the toxicity reducing effects of the colloidal metal, this treatment regimen has fewer side effects than conventional therapies. Additionally, because the biologically-active factor is internalized within the cell, this targeted delivery system can be used for gene therapy.

Through the use of this targeted delivery system, biologically-active factors which do not bind receptors on the cell surface can be delivered inside cells through selective generation of custom complexes that contain one or more such factors with at least one target molecule that is capable of binding to receptors on the cell surface. Such factors include, but are not limited to, chemotherapeutic drugs, nucleotides, and compositions for the treatment of immune diseases. Once the target molecule has bound to the receptor on the cell membrane, the entire complex, including both the target molecule and the biologically active factor are internalized. This method provides a simple, straightforward method for the intracellular treatment of diseases which were previously difficult to accomplish.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

This example demonstrates that colloidal gold neutralizes otherwise toxic substances and allows for an antibody response. When IL-2 (1 mg per 3 kg animal) is administered to three rabbits every third day for a two-week period, all the animals appear to be clinically sick, and two of the animals died from the apparent toxic effects of the IL-2. When the same dose of IL-2 is combined with colloidal gold and then administered to three rabbits for the same two-week period, no toxicity is observed and a significant antibody response results in all three animals. A positive antibody response is defined as a three to fourfold increase in specific antibody reactivity, as determined by direct ELISA, comparing the post-immunization bleed with the pre-immunization bleed. A direct ELISA is done by binding IL-2 onto a microtiter plate, and determining the quantity of IgG bound to the IL-2 on the plate, by goat anti-rabbit IgG conjugated to alkaline phosphatase.

EXAMPLE 2

This example further demonstrates that colloidal gold neutralizes otherwise toxic substances and allows for an antibody response. Endotoxin or lipid A (25, 50, and 100 $\mu$g per 35 mg mouse) are administered by subcutaneous injection every fourth day over a two-week period. For ten mice, endotoxin is given "neat" and for the remaining ten, the endotoxin is mixed 1:1 with colloidal gold. The injection volume is made up by adding potassium carbonate/sodium citrate buffer, pH 6.5 at a 1:1 dilution. The same protocol is also used where lipid A is the test drug.

The animals are checked at 15, 30, and 60 minutes following each injection, and then hourly and daily. The surviving animals are tested for a specific antibody response to the toxic substance they were injected with, either endotoxin or lipid A. Most of the animals injected with endotoxin or lipid A combined with colloidal gold survived, while those injected with the neat endotoxin or lipid A died during the two-week test period. In addition, those animals that did survive did have an antibody response to the specific toxin as determined by direct ELISA.

EXAMPLE 3

This example illustrates the effect of colloidal gold on cytokine activity in vivo. A group of mice are given IL-2 at a dose close to that given to cancer patients undergoing immunotherapy. In previous experiments, 18 $\mu$g of IL-2 tablets given to nude mice reduced implant tumor size, but killed the animals within two weeks. See Paciotti, G. F., and Tamarkin, L., Interleukin-2 Differentially Effects the Proliferation of a Hormone-Dependent and a Hormone-Independent Human Breast Cancer Cell Line In Vitro and In Vivo, *Anti-Cancer Research*, 8: 1233–1240 (1988), which is hereby incorporated by reference.

The efficacy of gold in a murine model system is tested in the following procedure: a group of mice are treated with IL-2 alone, IL-2 mixed with colloidal gold, colloidal gold alone, or saline solutions delivered through an osmotic mini pump. The mice are treated for seven days, after which they are sacrificed and their lymphocytes harvested. The cells are stained for T-cell or B-cell markers using specific murine monoclonal antibodies for flow cytometric analysis. Activated T- and B-cells are determined by assessing T-cell numbers, helper T-cell to suppresser T-cell ratios, activated cellular IL-2 receptor, B-cell numbers, and natural killer cell ("NK") numbers.

The few animals that survived being treated with IL-2 alone showed an increase in the T-cell number and activity (as determined by IL-2 receptors). Virtually all the animals survived IL-2 treatment in combination with colloidal gold, and these animals showed an increase in both B-cell function (as determined by activated B-cells and total IgG, measured by direct ELISA) an increase in T-cell function (as determined by T-cell number, and activity, using IL-2 receptor numbers as an index of activity), and an increase in NK activity.

EXAMPLE 4

The following biological experiment shows that colloidal gold reduces the toxicity of lipopolysaccharide (LPS). LPS is the lipid/sugar moiety of bacterial cell walls. When injected into an animal, this molecule mimics many of the clinical responses of septic shock. Thus, mice were injected with varying amounts of LPS in the presence or absence of colloidal gold. Specifically Balbic mice were injected with either 100 or 400 $\mu$g of LPS (strain *W.E. coli* 055:B5; 10 mg/ml in water; Difco Labs) with or without colloidal gold. The pH of the 15 nm colloidal gold mixture (E.Y. Labs) was adjusted to approximately 10, while the pH of the LPS was adjusted to 8 with 0.1 N NaOH. Subsequently, appropriate volumes (i.e., 10 µl for the 100 µg dose and 40 µl for the 400 µg dose) was then added to 500 µl of colloidal gold. The mixture was allowed to stand for 30 minutes and subsequently injected (i.p.) into the mice.

Within 12 hours after the injections, all mice exhibited clinical signs of depression and anergasia. Within 24 hours after the injection control mice in the 400 µg dose began to die. By 72 hours all of the control mice in the 400 µg dose died while 75% of the gold treated mice were alive and began showing signs of clinical improvement (i.e., movement). Furthermore, although subjective, the mice in the 100 µg dose which were treated with gold were more active throughout the 36 hours of observation.

EXAMPLE 5

The following experiment describes the use of colloidal gold as a putative adjuvant for generating mouse antibodies against murine IL-6. This experiment was performed with two goals in mind: First, to determine if colloidal gold could be used as an adjuvant in generating an immune response to "self antigens" (i.e., generating an immune response to a mouse protein using a mouse model); Second, since IL-6 is one of the cytokines thought to be involved in cancer cachexia, metastasis and sepsis, then the ability to generate antibodies in an autologous system may prove advantageous in generating a vaccine to the IL-6 and similar endogenous compounds.

Briefly described, the experiment is as follows. Several mice were immunized with colloidal gold/murine IL-6 mixture as described above. Approximately 3 weeks later, the mice were sacrificed and trunk blood was collected and analyzed for the presence of antibodies to murine IL-6 by a direct ELISA, as described above. The results from the direct ELISA, the determination of the serum antibody titers in mice immunized with murine IL-6 combined with colloidal gold, are illustrated in FIG. 1. FIG. 1 demonstrates that the mice had generated an antibody response to murine IL-6 thus indicating that the gold is be useful in generating antibodies to endogenous (i.e., self) toxins as well as cytokines thought to be involved in sepsis, cancer cachexia and metastasis.

Based upon these results, colloidal gold can also be used to generate monoclonal antibodies in transgenic mice through an immune response to "self antigens." Any colloidal gold bound antigen can be used to immunize the transgenic mice, resulting in the in vivo generation of Mabs.

EXAMPLE 6

The following experiment shows that cytokines mixed with colloidal gold retain their biological activity. The model used for these experiments is one which is well known in the art. See Paciotti, G. F., and L. Tamarkin, *Interleukin 1 directly regulates hormone-dependent human breast cancer cell proliferation in vitro, Mol. Endocrinol.,* 2: 459–464, 1988; and Paciotti, G. F., and L. Tamarkin, *Interleukin-1 differentially synchronizes estrogen-dependent and estrogen-independent human breast cancer cells in the GoIG I-phase of the cell cycle, AntiCancer Research,* 11: 25–32, 1991. The model is based on the ability of the cytokine, IL-1, to directly inhibit the growth of estrogen-responsive human breast cancer cells, MCF-7. Briefly described, IL-1 alone inhibits the growth of these cells through a well-characterized IL-1 receptor on the surface of these breast cancer cells.

Figure 4:
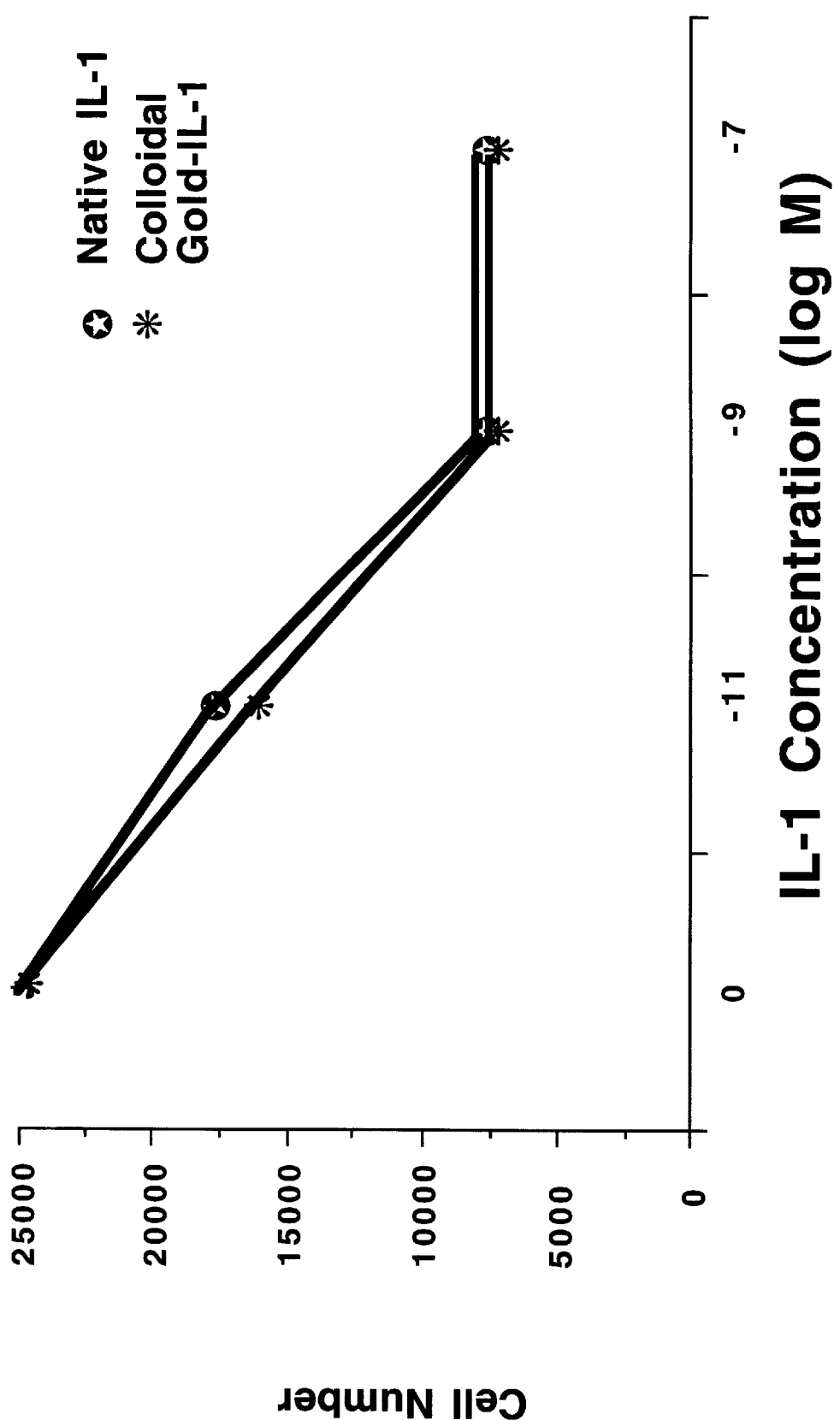
FIG. 4 illustrates the retention of biologic activity of IL-I after treatment with gold.

The following experiment shows the ability of IL-1 when mixed with colloidal gold to retain its biological activity by determining its ability to inhibit the growth of these cells. Approximately 8,000 MCF-7 cells were plated in 24-well tissue culture plates. On the next day, 15 nm gold particles were centrifuged at 14,000 rpm for 10 minutes and resuspended in sterile water. Human IL-α was reconstituted in water to an initial stock of $5\times10^{-5}$M in water. The pH of the gold and IL-1 was adjusted to approximately 8.0 with 0.1 M NaOH. Prior to mixing, the IL-1 was diluted to a working stock of $2\times10^{-6}$, $2\times10^{-8}$ M, and $2\times10^{-10}$ M, which contained 250 µl of the gold (final volume=0.5 ml). Gold controls consisted of 250 µl of gold and 250 µl of sterile water. Subsequently, each working stock was further diluted 1/20 in tissue media resulting in final concentrations of $10^{-7}$, $10^{-9}$, and $10^{-11}$ M. These solutions along with the appropriate controls were then added directly to the MCF-7 cells. The data presented in FIG. 4 are the number of cells present at various days after the addition of IL-1 with or without the gold.

EXAMPLE 7

Figure 3:
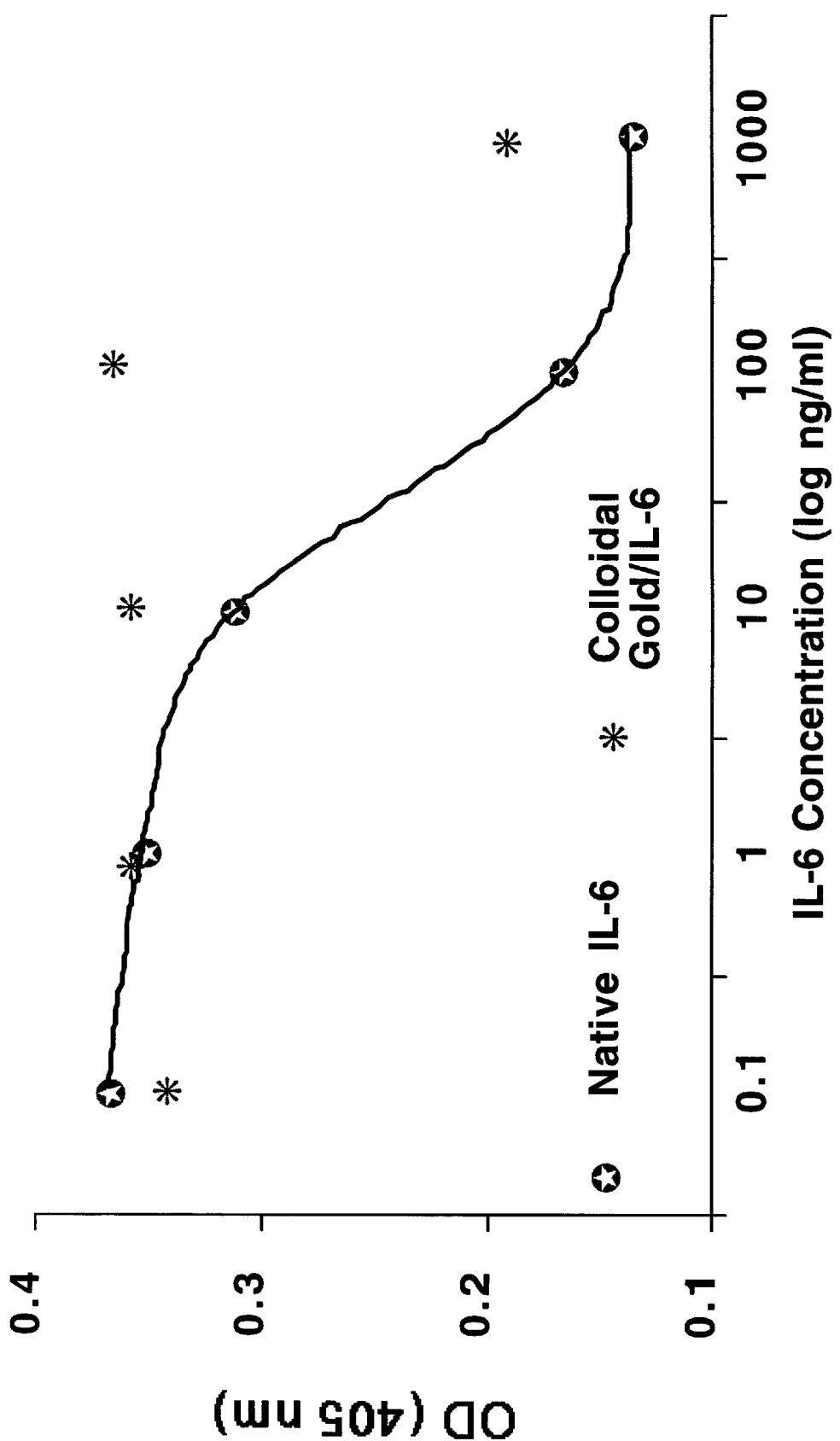
FIG. 3 illustrates the efficiency with which gold binds IL-6.

The following experiment shows the efficiency with which gold binds cytokine. This experiment demonstrates that the protein is removed from the solution when it is combined with gold and then centrifuged. The experiment used the IL-6 standard from ARI's Cytokit-6. Prior to mixing, the pH of the gold and cytokine solutions were adjusted to pH 9 with 0.1 N NaOH. This protein was either preincubated with gold or water prior to using it in ARI's diagnostic kit for IL-6. Following this incubation, the colloidal gold IL-6 mixture was centrifuged and the supernatants were used to generate a standard curve. As can be seen from FIG. 3 the gold was very effective at binding virtually all the IL-6 in the dose-range of the assay, removing the IL-6 from the supernatant. Even at the highest final concentration (1000 ng/ml) of IL-6, the gold removed approximately 90% of the IL-6 in the solutions. This amount is based on the OD of the 1000 ng/ml IL-6 /gold supernatant, which is similar to the 100 ng/ml IL-6 standard alone.

EXAMPLE 8

The following experiment shows the physical changes in the gold colloid solution upon its mixing with IL-6, a potential antigen for a vaccine. Although the gold particles are approximately 15 nm in size, they cannot be filtered through a 0.22 µm syringe filter. We attribute this to the nature of the gold particles in this colloid mixture. It is theorized that the gold as a colloidal mixture forms aggregates larger than the individual spheres. Although the individual particles are smaller than the pore size of the filter, the aggregates are much larger and thus are not filterable. However, we observed that once the colloidal gold is incubated with protein it easily filters through the 0.22 µm filter. Thus, the binding of a cytokine appears to change the physical interactions of the gold particles with each other; making the gold particles act as single 15 nm particles and enabling the particles to be readily filtered. This experiment defines the nature of the binding of an antigen to the colloidal metal.

EXAMPLE 9

Figure 5:
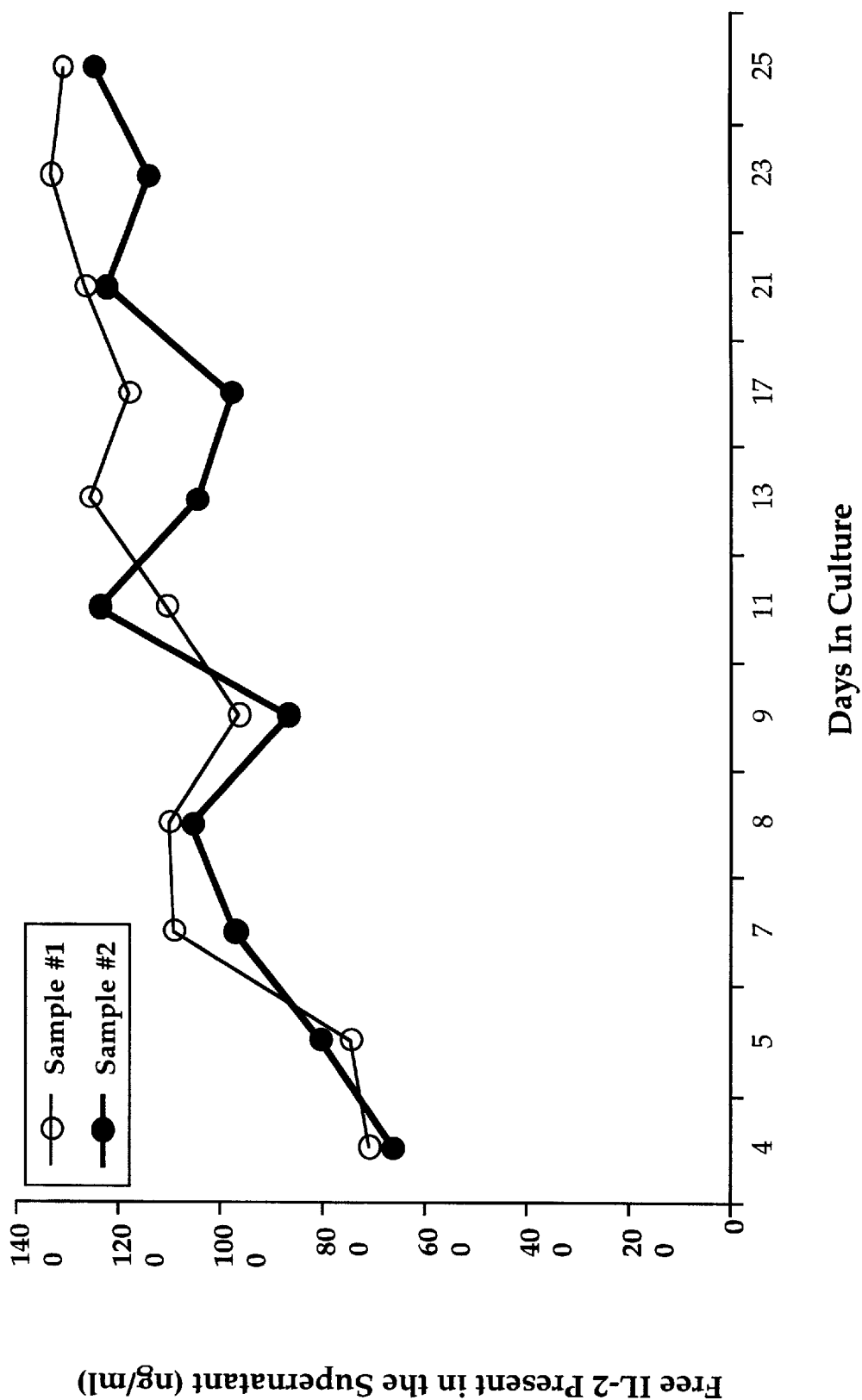
FIG. 5 illustrates the effect of ti me on the release of IL-2 from colloidal gold.

Human IL-2 was reconstituted in water at a pH of 11. 200 µg of IL-2 was incubated with 25 ml colloidal gold for 24 hours. The colloidal gold bound IL-2 solution was then centrifuged at 14,000 rpm for 20 minutes in a microcentrifuge at room temperature. The supernatant was then removed from the pellet. The IL-2 complex was then placed into each well of 24 well plates and incubated at 37° C. for 25 days. Samples were removed from the wells on days 4, 5, 7, 8, 9, 11, 13, 17, 21, 23, and 25. The samples were centrifuged to remove colloidal gold:IL-2 complex. The supernatants were frozen. After the last sample was collected and frozen, all of the samples were batch analyzed in CytImmune Science, Inc.'s CytELISA-2 sandwich EIA for IL-2 . The results of this assay are in FIG. 5.

EXAMPLE 10

Human TNFα was reconstituted in water at a pH of 11. 200 µg of the TNFα was incubated with the colloidal gold for 24 hours. The TNFα:colloidal gold solution was then centrifuged at 14,000 rpm for 20 minutes in a microcentrifuge at room temperature. The supernatant was then removed from the pellet.

Figure 6:
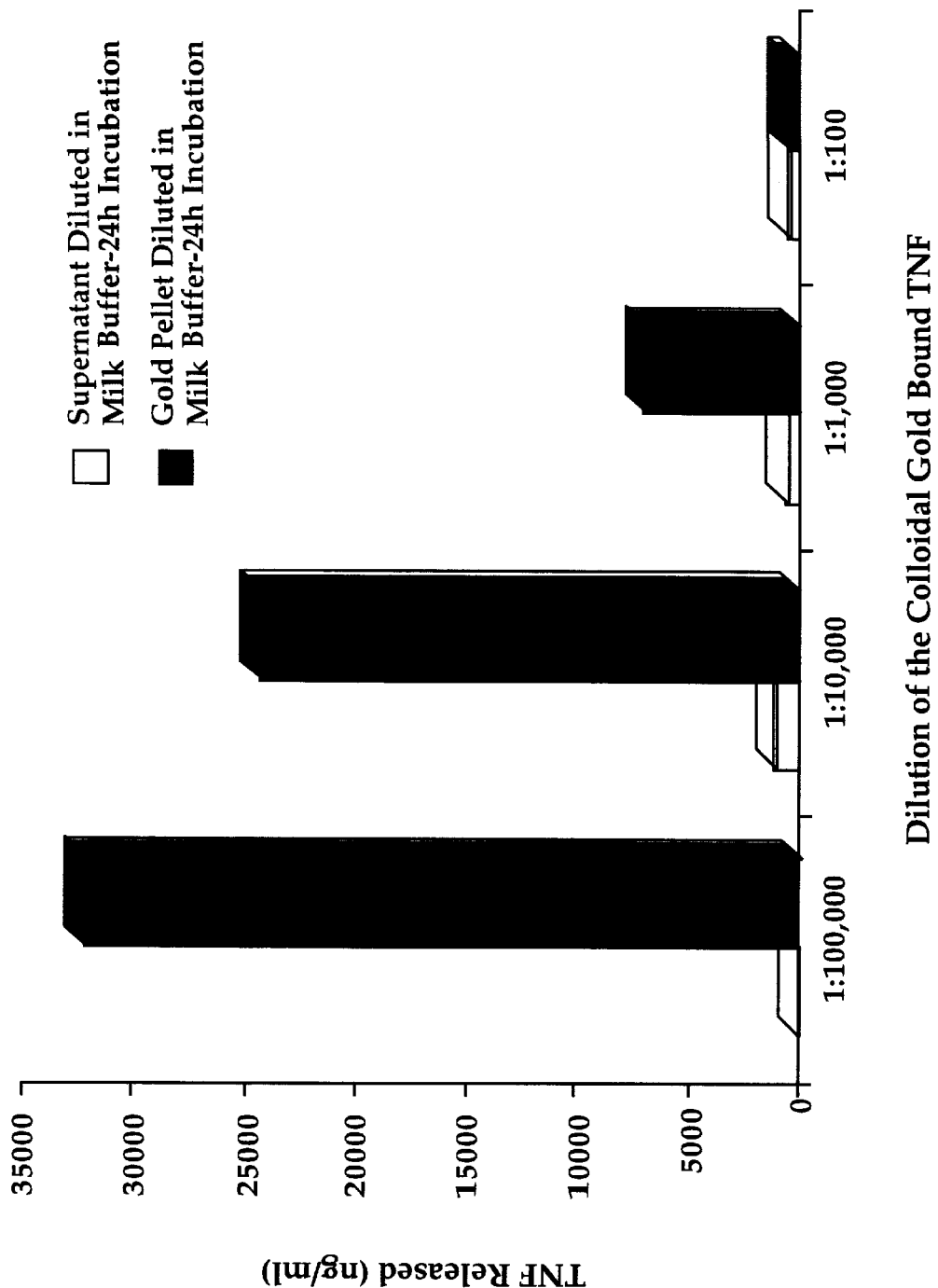
FIG. 6 illustrates the effect of dilution on the release of TNFα from colloidal gold.

The pellet was reconstituted in 1 ml of water and diluted in milk buffer to achieve final concentrations of 1:100, 1:1,000, 1:10,000, and 1:100,000 and incubated for 24 hours at room temperature. The samples were then subjected to analysis using CytImmune Sciences, Inc.'s CytELISA TNFα assay. The results of this assay are in FIG. 6.

This experiment shows that as a result of the dilution, the colloid releases more of the cytokine which is bound to it. Thus, cytokine binding and release by colloidal gold exhibits equilibrium kinetics applicable to in vivo situations involving the continuous dilution of the colloidal gold by blood and extracellular fluids.

EXAMPLE 11

Figure 7:
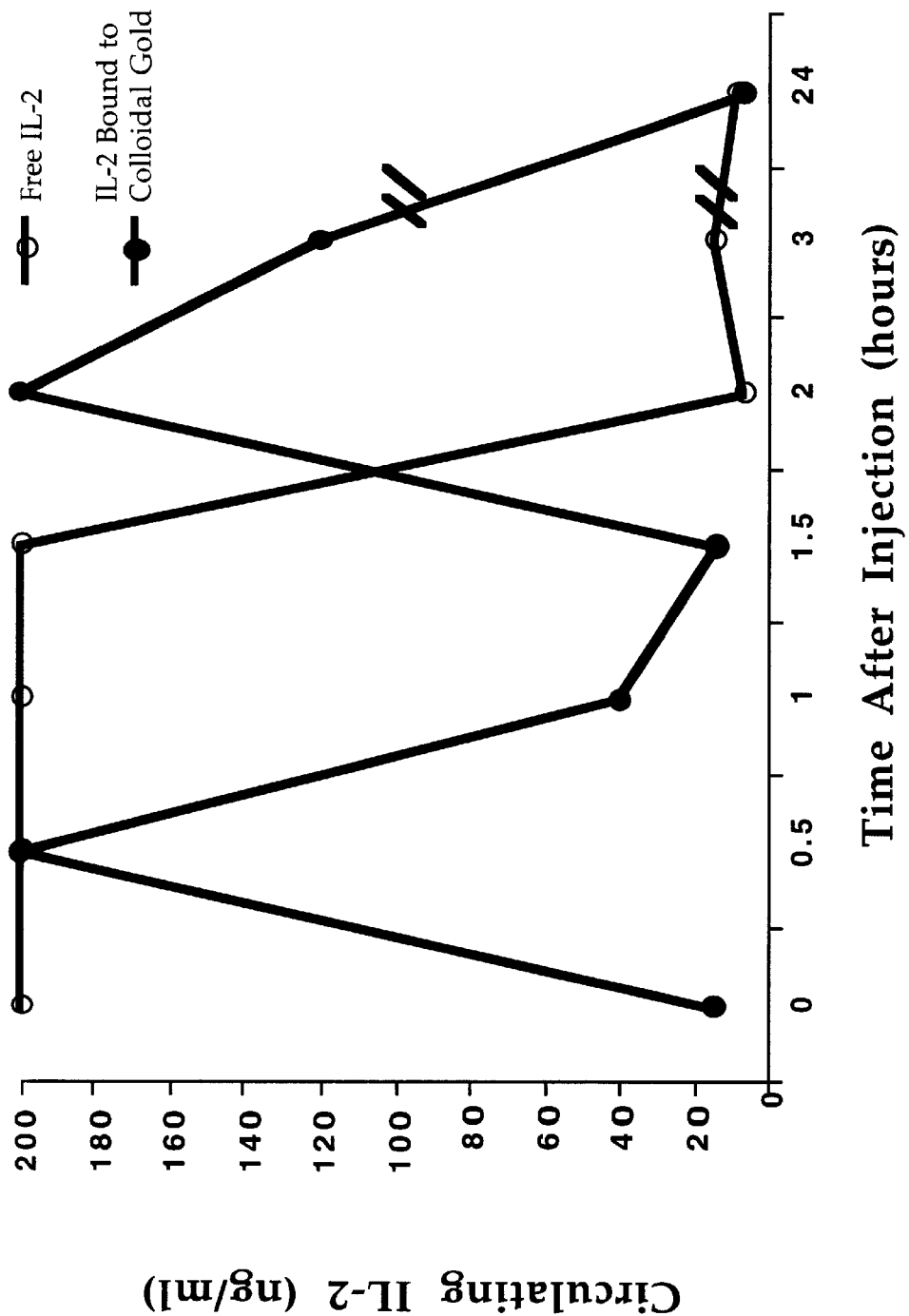
FIG. 7 illustrates the in-vivo release of IL-2 bound to colloidal gold.

500 µg of recombinant IL-2 was dissolved in 0.5 ml of pH=11 water. The solution was then added to 25 ml of colloidal gold by the method described in Example 9. Balb/C mice were injected (i.p.) with either 0.1 ml of the colloidal gold bound IL-2 or 100 µg of neat IL-2 . The mice (4 mice/group/time point) were sacrificed at various time points (0, 0.5, 1.0, 1.5, 2.0, 3.0 and 24 hr) after injection, and trunk blood was collected. The resultant sera was analyzed in CytImmune Sciences, Inc.'s competitive EIA for IL-2 . Over the time points tested, the release of IL-2 from the colloidal gold appeared to have a bimodal pattern. (FIG. 7) One explanation for this may be the equilibrium of IL-2 released from the colloidal gold into the abdomen chich, subsequently equilibrated with the blood pools.

EXAMPLE 12

50,000 MCF-7 cells were plated in each well of a 6-well plate in 2 ml of phenol-red-free IMEM WITH 10% CSS. The cells were allowed to grow until they were 70–80% confluent. 200 µg of IL-1β was bound to colloidal gold using the method described in Example 9. After binding, the complexed material was centrifuged and blocked with 1% HSA solution. 100 ul of colloidal gold-bound IL-1β complex was added to each well and incubated for 1 to 5 days. The cells were then washed with phenol-red-free IMEM with 10% charcoal-stripped fetal bovine serum (FBS). The binding of the colloidal gold:IL-1β complex to the MCF-7 cells was detected by visualization of the colloidal gold on the cell surface using bright field and phase contrast microscopy. The Colloidal gold/IL-1β remaining on the cell surface was visualized by fluorescence microscopy using rabbit anti-human IL-1β which was internalized into the cells was determined as a negative signal between the fluorescence and bright field images. The results of this assay are illustrated in FIG. 8.

Figure 8B:
Figure 8C:
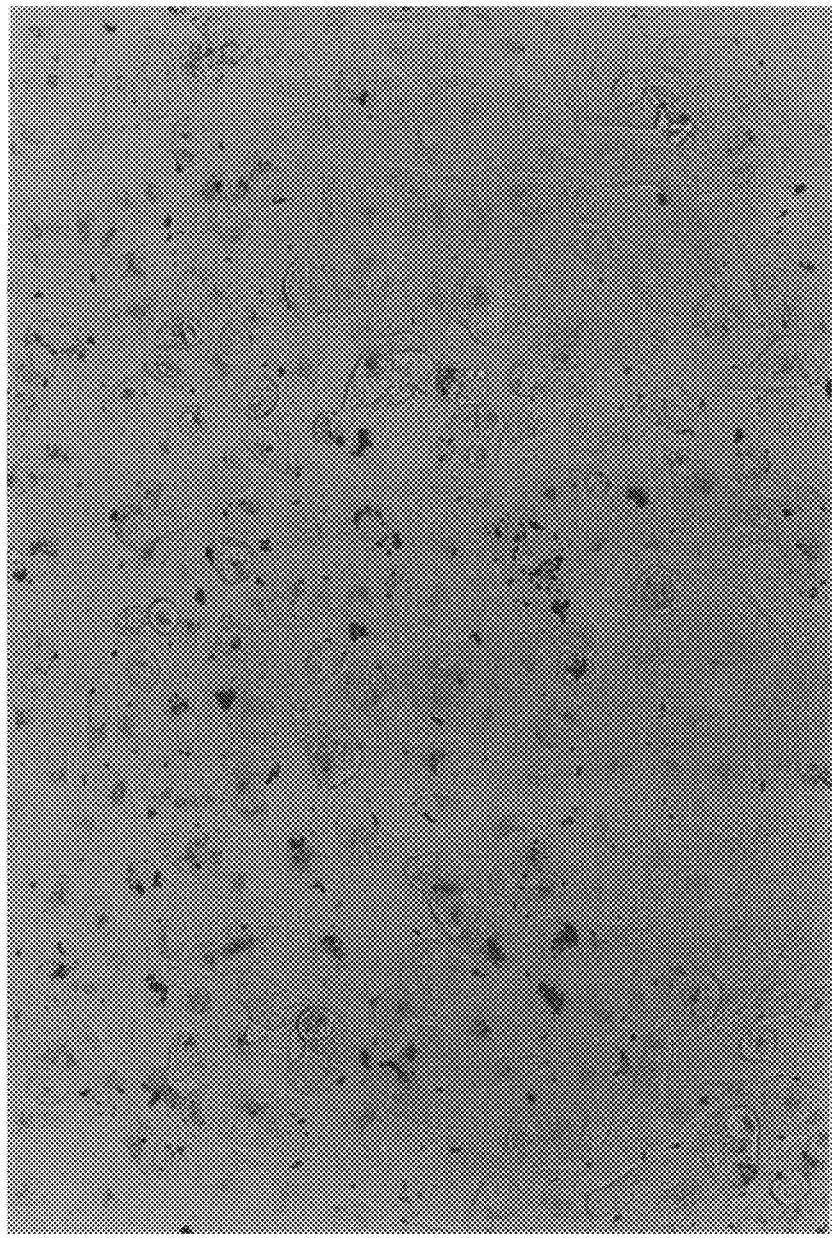
Figure 8D:

FIG. 8a is the bright field view of untreated MCF-7 cells (control), and FIG. 8b depicts the background fluorescence from the non-specific binding of FITC conjugated antibodies. FIG. 8b illustrates the bright field view for MCF-7 cells treated with colloidal gold bound IL-1β, and FIG. 8d illustrates FITC fluorescence for MCF-7 cells treated with colloidal gold bound IL-1β complex and internalization of the complex. Some of the colloidal gold:IL-1b complex in these figures is bound to the cell membrane, as indicated by the bright spots, and some has been internalized within the cell, as indicated by the dark spots.

This example shows that one can bind colloidal metal:biologically active factor complex to receptors on the cell surface and that the complex is subsequently internalized within the cell.

EXAMPLE 13

50,000 MCF-7 cells were plated in each well of a 6-well plate in 2 ml of phenol-red-free IMEM with 10% CSS. The cells were allowed to grow until they were 70–80% confluent. The cells were then treated with either media, 0.5 µg/ml TNFα, 5.0 µg/ml TNFα, or 50 µg/ml TNFα, 0.5 µg/ml IL-1 β, 5.0 µg/mil IL-1β, or 50 µg/ml IL-1 β.

100 ug of IL-1β was bound to colloidal gold by the method described in Example 9. After binding, the complexed material was centrifuged and blocked with 1% HSA solution. 100 ul of colloidal gold bound IL-1β complex was added to each well and incubated for 24–48 hours. The cells were then washed with phenol-red-free IMEM with 10% CSS. The binding of the IL-1β:colloidal gold:TNFα di-cytokine to the MCF-7 cells was detected by visualization of the colloidal gold on the cell surface using bright field or fluorescence microscopy.

These data indicate that colloidal gold can simultaneously bind two or more biologically-active factors, allowing for the generation of custom complexes which can bind to the cell membrane and provide a targeted drug delivery system.

EXAMPLE 14

100 ug each of IL-6 , IL-1β and TNFα were simultaneously bound to the same colloidal gold solution using the method described in Example 9. After centrifugation and blocking with HSA solution, the samples were used as unkowns in CytImmune Sciences, Inc.'s sandwich assay for TNF-α. In this assay a monoclonal antibody was used to capture TNF-α in the sample. The monoclonal antibody bound TNF-α was then detected with a rabbit-anti-human TNF-α antibody followed by an enzyme labeled goat-anti-rabbit antibody.

Figure 9:
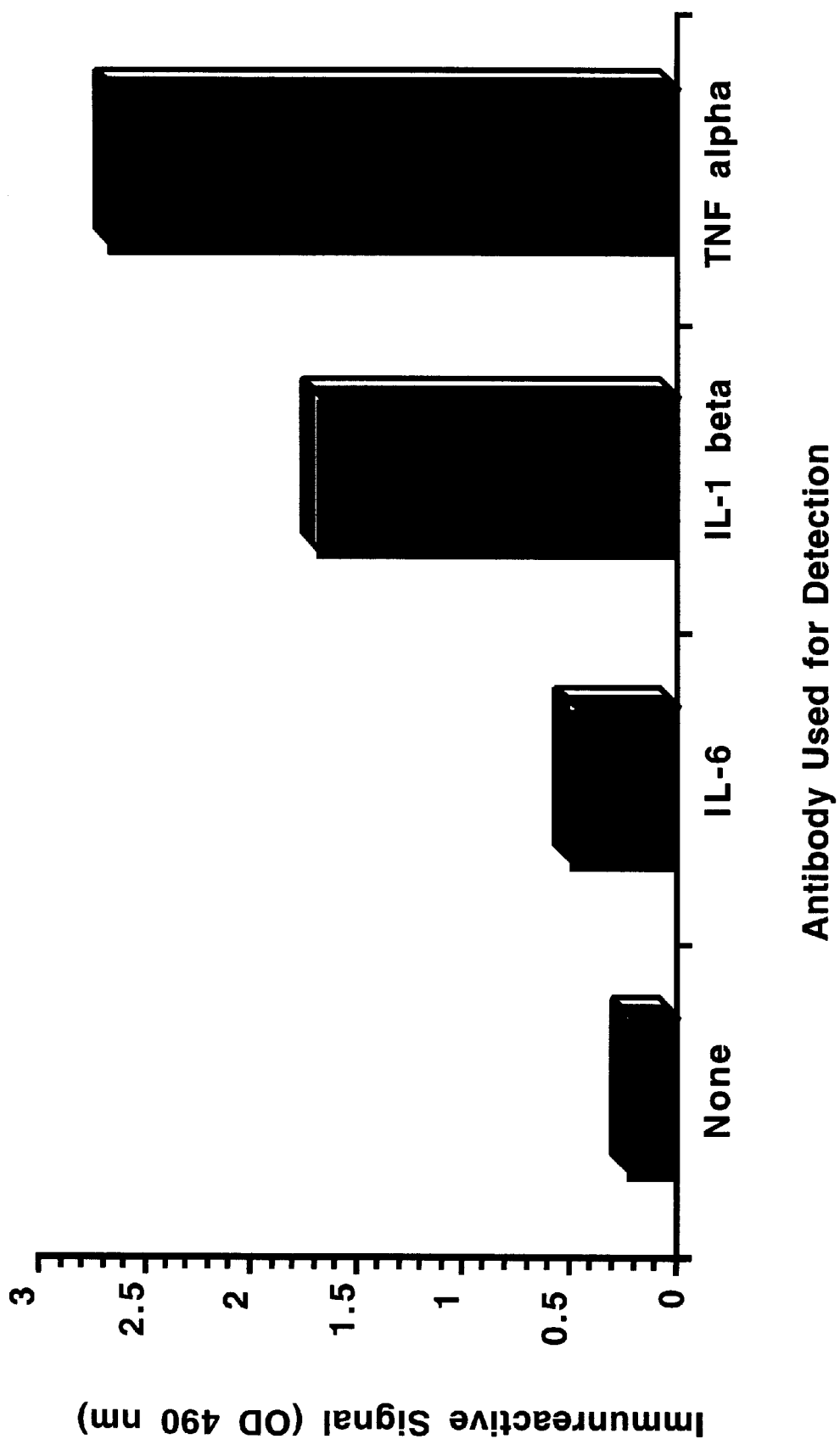
FIG. 9 illustrates the effect on immunoreactivity of colloidal gold which is coupled with TNFα, IL-6 and IL-1β.

To demonstrate that the same colloidal gold particle bound all IL-6 , IL-1β and TNF-α, the monoclonal antibody to TNF-α was used to capture 3 sets of quadruplicate samples containing colloidal gold particles which had been simultaneously coated with TNF-α, IL-6 and IL-1 β. To demonstrate the tri-cytokine particle, one set of samples was detected with the TNF-α polyclonal antibody, another with the IL-6 polyclonal antibody, and the other with the IL-1β polyclonal antibody. All of the samples were subsequently detected with goat-ant-rabbit antibodies. As, predicted, the colloidal gold bound TNF-α was easily captured and detected with the TNF-α monoclonal/polyclonal antibody binding pairs. In addition, the same samples exhibited a significant amount of immunoreactivity for IL-6 and IL-1β, which was only possible if the three cytokines were bound to the same particles. The results of this assay are illustrated in FIG. 9.

These data indicate that colloidal gold can simultaneously bind two or more biologically-active factors, allowing for the generation of custom complexes which can bind to the cell membrane and provide a targeted drug delivery system. These custom complexes can also be used to immunize transgenic mice, generating an immune response to "self antigens" and the production of multiple Mabs. For example, the custom complexes from this experiment could be used to elicit the simultaneous generation of TNF-α, IL-6 and IL-1β Mabs.

It should be understood, of course, that the foregoing relates only to specific examples of the present invention and that numerous modifications or alterations may be made therein without departing from the spirit and the scope of the invention as set forth in the appended claims.

What is claimed is:

1. A composition capable of targeting a particular tissue comprising a biologically-active factor selected from the group consisting of TNF-α and lymphotoxin and a target molecule admixed with or bound to a colloidal metal.

2. The composition of claim 1, wherein the colloidal metal is selected from the group consisting of colloidal gold and a colloidal silver.

3. The composition of claim 1, wherein the biologically-active factor is Tumor Necrosis Factor ("TNFα").

4. The composition of claim 1, further comprising a pharmaceutically-acceptable component selected from the group consisting of excipients, buffers, antigen stabilizers, and sterilized carriers.

5. The composition of claim 1, further comprising a pharmaceutically-acceptable adjuvant.

6. The composition of claim 5, wherein the adjuvant is selected from the group consisting of Freund's Complete, lipopolysaccharide, monophosphoryl lipid A, muramyl dipeptide, liposomes containing lipid A, alum, muramyl tripeptide-phosphatidyl-ethanoloamine, keyhole limpet hemocyanin, and Freund's Incomplete Adjuvant.

7. The composition of claim 1, further comprising additional biologically-active factors admixed with or bound to the colloidal metal.

8. A method of administering a biologically-active factor to a human or animal comprising:

1) admixing or binding a biologically-active factor selected from the group consisting of TNF-α and lymphotoxin and a target molecule with a colloidal metal to form a composition; and 2) administering the composition to the human or animal.

9. The method of claim 8, wherein the biologically-active factor is tumor necrosis factor ("TNFα").

10. The method of claim 8, wherein the composition further comprises additional biologically-active factors admixed with or bound to the colloidal metal.

11. A method of treating a human or animal with a cancer or immune disease comprising administering to the human or animal with the cancer or immune disease a therapeutically effective amount of a composition capable of targeting a particular tissue comprising a biologically-active factor selected from the group consisting of TNF-α and lymphotoxin and a target molecule admixed with or bound to a colloidal metal.

12. The method of claim 11, wherein the biologically-active factor is tumor necrosis factor ("TNF-α").

13. The method of claim 11, wherein the composition is administered in a single dose.

14. The method of claim 11 wherein the composition is administered in multiple doses.

15. The method of claim 11, wherein the target molecule is selected from the group consisting of Interleukin-1 ("IL-1"), Interleukin-2 ("IL-2"), Interleukin-3 ("IL-3"), Interleukin-4 ("IL-4"), Interleukin-5 ("IL-5"), Interleukin-6 ("IL-6 "), Interleukin-7 ("IL-7"), Interleukin-8 ("IL-8"), Interleukin-10 ("IL-10"), Interleukin-i 1 ("IL-11"), Interleukin-12 ("IL-12"), Interleukin-13 ("IL-13"), Type I Interferon, Type II Interferon, Tumor Necrosis Factor ("TFNα")), Transforming Growth Factor-β ("TGF-β"), vascular epithelial growth factor ("VEGF"), receptor proteins, glucose, glycogen, phosphoipids, monoclonal and/or polyclonal antibodies, and transforming growth factor ("TGFα").

16. The method of claim 11, wherein the composition further comprises additional biologically-active factors admixed with or bound to the colloidal metal.

17. A method for the delivery of more than one biologically-active factor comprising administering to a human or animal a composition comprising more than one biologically-active factor selected from the group consisting of TNF-α and lymphotoxin and a target molecule admixed with or bound to a colloidal metal.

18. The method of claim 17, wherein the biologically active factor is tumor necrosis factor ("TNFα").

19. The method of claim 17, wherein the target molecule is selected from the group consisting of Interleukin-1 ("IL-1"), Interleukin-2 ("IL-2"), Interleukin-3 ("IL-3"), Interleukin-4 ("IL-4 "), Interleukin-5 ("IL-5"), Interleukin-6 ("IL-6 "), Interleukin-7 ("IL-7"), Interleukin-8 ("IL-8"), Interleukin-10 ("IL-10"), Interleukin-11 ("IL-11"), Interleukin-12 ("IL-12"), Interleukin-13 ("IL-13"), Type I Interferon, Type II Interferon, Tumor Necrosis Factor ("TFNα"), Transforming Growth Factor-β ("TGF-β"), vascular epithelial growth factor ("VEGF"),receptor proteins, glucose, glycogen, phosphoipids, monoclonal and/or polyclonal antibodies, and transforming growth factor alpha ("TGFα").

20. A method of treating a human or animal with a cancer comprising administering to the human or animal with the cancer a therapeutically effective amount of a composition comprising a biologically-active factor selected from the group consisting of TNF-α and lymphotoxin admixed with or bound to a colloidal metal.

21. A method of treating a human or animal with a cancer or immune disease comprising administering to the human or animal with the cancer or immune disease a therapeutically effective amount of a composition comprising a biologically-active factor which is tumor necrosis facto ("TNFα") admixed with or bound to a colloidal metal.

* * * * *